US011484265B2

(12) United States Patent
Wang et al.

(10) Patent No.: US 11,484,265 B2
(45) Date of Patent: Nov. 1, 2022

(54) ADHESIVE DEVICE

(71) Applicant: BioIntelliSense, Inc., Golden, CO (US)

(72) Inventors: David Jonq Wang, Palo Alto, CA (US); James R. Mault, Evergreen, CO (US); Eleanor Drake, Daly City, CA (US); Henry WeiKang Leung, Sunnyvale, CA (US); Brian Chris Ro, Foster City, CA (US)

(73) Assignee: BIOINTELLISENSE, INC., Golden, CO (US)

( * ) Notice: Subject to any disclaimer, the term of this patent is extended or adjusted under 35 U.S.C. 154(b) by 666 days.

(21) Appl. No.: 16/433,816

(22) Filed: Jun. 6, 2019

(65) Prior Publication Data

US 2020/0383639 A1 Dec. 10, 2020

(51) Int. Cl.
*A61B 5/145* (2006.01)
*A61B 5/00* (2006.01)
*A61B 5/1477* (2006.01)
*A61B 10/02* (2006.01)

(52) U.S. Cl.
CPC .......... *A61B 5/6833* (2013.01); *A61B 5/1477* (2013.01); *A61B 5/14517* (2013.01); *A61B 5/4845* (2013.01); *A61B 10/02* (2013.01); *A61B 2560/0412* (2013.01); *A61B 2562/0295* (2013.01); *A61B 2562/066* (2013.01)

(58) Field of Classification Search
CPC ........... A61B 5/00; A61B 10/02; A61B 5/145; A61B 5/1477; A61B 5/6833; A61B 5/14517; A61B 5/4845; A61B 2562/0295; A61B 2562/066; A61B 2560/0412
See application file for complete search history.

(56) References Cited

U.S. PATENT DOCUMENTS

| | | | |
|---|---|---|---|
| 2003/0113906 A1* | 6/2003 | Sangha | C12Q 1/6806 435/287.2 |
| 2004/0219537 A1 | 11/2004 | Fenrich et al. | |
| 2007/0179373 A1 | 8/2007 | Pronovost | |
| 2012/0310070 A1 | 12/2012 | Kumar et al. | |
| 2016/0256070 A1 | 9/2016 | Murphy et al. | |
| 2017/0027482 A1* | 2/2017 | Zilberstein | A61B 5/082 |
| 2017/0231571 A1* | 8/2017 | Rogers | A61B 5/002 600/301 |
| 2017/0340274 A1* | 11/2017 | Lambert | A61B 5/4875 |

(Continued)

OTHER PUBLICATIONS

Zhang et al., "Passive sweat collection and colormetric analysis of biomarkers relevant to kidney disorders using a soft microfluidic system" Lab on a Chip, Mar. 12, 2019, pp. 1545-1555.

(Continued)

*Primary Examiner* — Eric J Messersmith
(74) *Attorney, Agent, or Firm* — Maschoff Brennan

(57) ABSTRACT

An adhesive device may include a first adhesive surface configured to be adhered to skin of a user, and a second adhesive surface opposite the first adhesive surface and configured to be adhered to a medical device. The adhesive device may also include an intermediate region between the first adhesive surface and the second adhesive surface, where the intermediate region includes a detector compound embedded in the intermediate region configured to change based on interaction of the detector compound with a target molecule.

20 Claims, 10 Drawing Sheets

(56) References Cited

U.S. PATENT DOCUMENTS

| | | |
|---|---|---|
| 2018/0184939 A1 | 7/2018 | Christiansen et al. |
| 2018/0263543 A1 | 9/2018 | Harttig et al. |
| 2019/0000355 A1* | 1/2019 | Costello .............. A61B 5/6898 |
| 2019/0000357 A1 | 1/2019 | Ross |
| 2019/0282167 A1* | 9/2019 | Balczewski ............ A61B 5/282 |

OTHER PUBLICATIONS

International Search Report and Written Opinion issued in corresponding application No. PCT/US2020/036644, dated Oct. 21, 2020.

\* cited by examiner

ADHESIVE DEVICE

FIELD

Some embodiments described herein generally relate to an adhesive device.

BACKGROUND

Unless otherwise indicated herein, the materials described herein are not prior art to the claims in the present application and are not admitted to be prior art by inclusion in this section.

Monitoring devices to monitor a subject have been found to be beneficial for identifying information regarding the subject, such as heart rate, temperature, blood pressure, or other biological characteristics of the subject. Some monitoring devices can be worn, such as an electrocardiogram (ECG) lead, a blood pressure cuff, etc. However, such monitoring devices are often bulky or must be attached to some external machine that makes it such that the monitoring device is not mobile.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Some example embodiments described herein generally relate to an adhesive device that may be used to fixedly adhere a monitoring device to a subject for a period of time such as an entire day or multiple days.

In an example embodiment, an adhesive device may include a first adhesive surface configured to be adhered to skin of a user, and a second adhesive surface opposite the first adhesive surface and configured to be adhered to a medical device. The adhesive device may also include an intermediate region between the first adhesive surface and the second adhesive surface, where the intermediate region includes a detector compound embedded in the intermediate region configured to change based on interaction of the detector compound with a target molecule.

In another example embodiment, an adhesive device may include an adhesive film with an adhesive side configured to be adhered to skin and a non-adhesive side. The adhesive film may include a first surface area, and a first material configured to allow moisture to pass in one direction through the adhesive film from the adhesive side to the non-adhesive side while preventing moisture from passing through the adhesive film from the non-adhesive side to the adhesive side. The adhesive device may additionally include a pocket disposed upon the adhesive side the adhesive film, where the pocket is shaped to receive a monitoring device within the pocket such that the monitoring device avoids contact with the adhesive side of the adhesive film when disposed within the pocket. The pocket may include a second material configured to wick moisture away from the skin. Additionally, the pocket may cover a second surface area of the adhesive side of the adhesive film, where the second surface area covers one third of the first surface area or less.

Additional features and advantages of the disclosure will be set forth in the description which follows, and in part will be apparent from the description, or may be learned by the practice of the disclosure. Some of the features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawings. It is appreciated that these drawings depict only some embodiments of the disclosure and are therefore not to be considered limiting of its scope. The disclosure will be described and explained with additional specificity and detail through the use of the accompanying drawings in which.

DETAILED DESCRIPTION OF SOME EXAMPLE EMBODIMENTS

Some embodiments described herein generally relate to an adhesive device used to adhere a monitoring device to a subject. The adhesive device may provide additional functionality, outside of that provided by the monitoring device. For example, the adhesive device may include one or more detector compounds embedded within the adhesive device that permits the detection of various target molecules. The detector compounds may monitor for molecules such as the metabolites or other byproducts generated by the body when certain foods or drugs have been ingested or otherwise consumed. For example, the detector compounds may monitor for such byproducts and/or metabolites eluted in sweat. Such byproducts may include molecules such as cotinine (byproduct of nicotine), acetate and/or acetaldehyde (byproducts of ethanol), 9-carboxy THC (byproduct of cannabis), benzoylecgonine and/or ecgonine methyl ester (byproducts of cocaine), etc.

The adhesive device may be part of a system that includes the monitoring device. The monitoring device may be lightweight with a low profile such that it can be worn by the subject for days or weeks at a time without irritation. The monitoring device may include multiple sensors, such as a microphone oriented towards the skin of the subject, an accelerometer, a gyroscope, a thermometer, electrocardiogram (ECG) leads, etc.

As used herein, the term "subject" may refer to an individual wearing a monitoring device. The term "user" may refer to the subject or may refer to any other individual taking some action associated with embodiments of the present disclosure (e.g., a separate individual may assist the subject in adhering the monitoring device to the skin of the subject).

Reference will now be made to the drawings to describe various aspects of some example embodiments of the disclosure. The drawings are diagrammatic and schematic representations of such example embodiments, and are not limiting of the present disclosure, nor are they necessarily drawn to scale.

Figure 1:
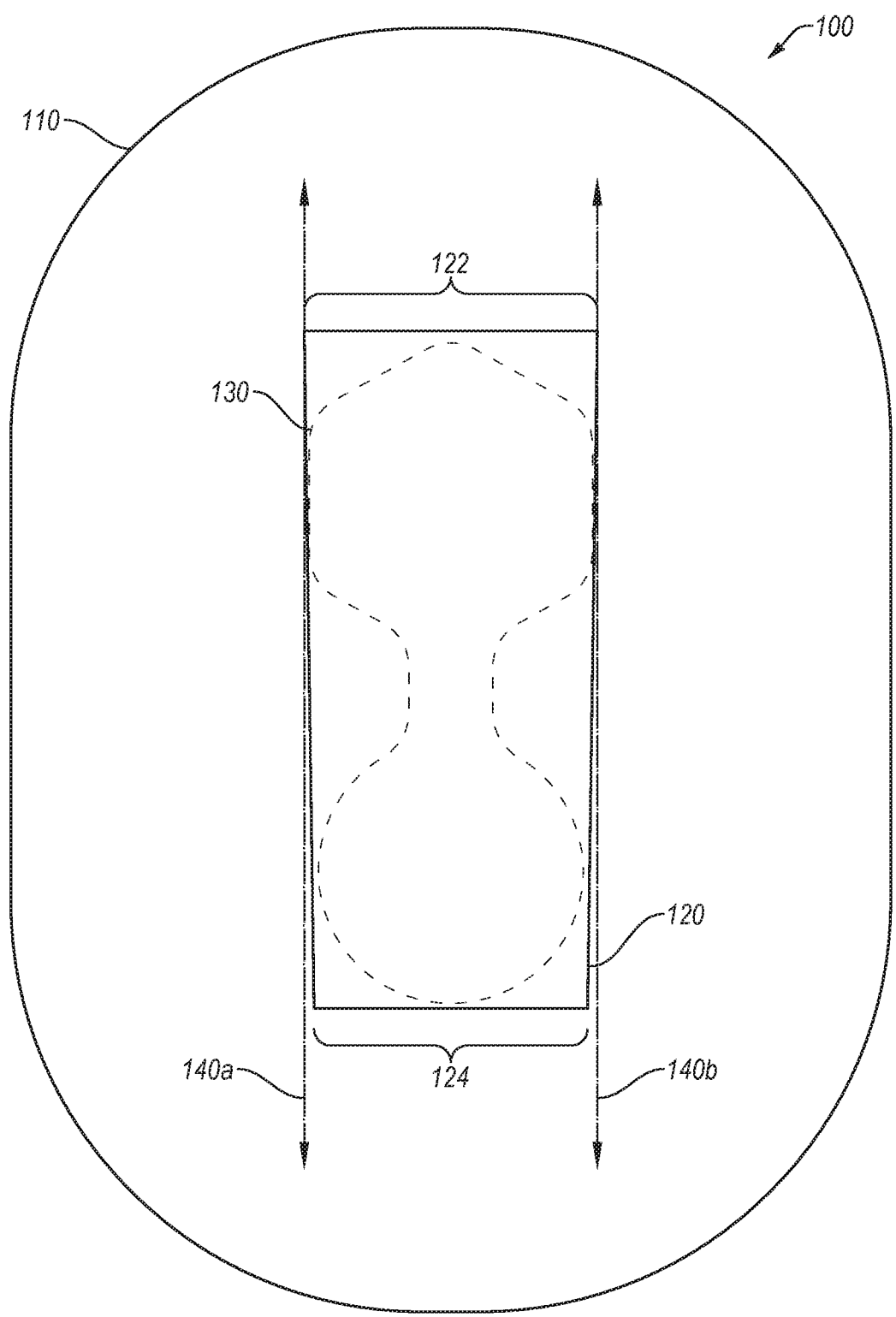
FIG. 1 illustrates an example adhesive device from a top down view.

FIG. 1 illustrates an example adhesive device 100 from a top down view (e.g., a view looking from the skin outwards), in accordance with one or more embodiments of the present disclosure. The adhesive device 100 may include an adhesive film 110, and a pocket 120 for receiving a monitoring device 130. The adhesive device 110 may operate to adhere the pocket 120 with the monitoring device 130 to the skin of a subject.

The adhesive film 110 may include any material with an adhesive side and a non-adhesive side. The adhesive side may operate to adhere the adhesive film 110 to the skin of the subject. The non-adhesive side may operate to act as an outer surface for the pocket 120 and/or the monitoring device 130. In some embodiments, the adhesive film 110 may be made of a material and/or otherwise contain properties such that moisture may pass from the skin side (e.g., the adhesive side of the adhesive film 110) to the side away from the skin of the subject (e.g., the non-adhesive side of the adhesive film 110). In this way, sweat or other moisture beneath the adhesive film 110 may be released to maintain comfort of the subject when having the adhesive film 110 adhered to the skin of the subject. Additionally or alternatively, the adhesive film 110 may be made of a material and/or otherwise contain properties such that moisture may not pass from the non-adhesive side of the adhesive film 110 to the adhesive side of the adhesive film 110. In some embodiments, the adhesive film 110 may permit the passage of oxygen and other air molecules through the adhesive film 110. The properties of the adhesive film 110 may facilitate the skin beneath the adhesive film 110 remaining healthy while the adhesive film 110 is adhered to the skin.

In some embodiments, the adhesive film 110 may be made of a material and/or use an adhesive that adheres to the skin of the subject for multiple days, and/or weeks. In some embodiments, the adhesive on the adhesive side of the adhesive film 110 may be configured to break down after approximately one week such that the adhesive film 110 may be removed with minimal discomfort due to the breakdown of the adhesive. In some embodiments the adhesive film 110 may be made of a silicone adhesive material. Additionally or alternatively, other materials may be used, such as a hydrogel. In some embodiments, the types of sensors on the monitoring device may contribute to a selection of the material for the adhesive material. For example, if the monitoring device 130 is configured to perform an EKG, the adhesive material may include a hydrogel.

As illustrated in FIG. 1, in some embodiments, the adhesive film 110 may have a generally capsule or ovoid shape. For example, the shape may include a regular curvature at either end with an extended straight portion therebetween. It will be appreciated that the adhesive film 110 may take any shape, such as a rectangular shape, a rounded rectangular shape, a circular shape, or any other shape. In some embodiments, the adhesive film 110 may be of any length and any width. For example, the adhesive film 110 may be between approximately 70 millimeters (mm) and 200 mm long, 100 and 150 mm long, or approximately 126 mm long. As another example, the adhesive film 110 may be between approximately 40 mm and 150 mm wide, 60 and 110 mm wide, or approximately 85 mm wide. In some embodiments, the width may be approximately two thirds of the length of the adhesive film 110.

The pocket 120 may be shaped and configured to receive the monitoring device 130. The pocket 120 may be located at approximately the middle of the adhesive film 110. The pocket 120 may be made of a material configured to wick moisture away from the skin. For example, the pocket 120 may be made of a non-woven material with both hydrophobic and hydrophilic components configured to draw moisture into the material and release the moisture from the material. In these and other embodiments, the pocket 120 may be made of a single piece of material with adhesive on one side of the material wrapped once or multiple times around an area to receive the monitoring device 130 such that the pocket 120 may include adhesive on a skin-facing side of the pocket 120. In some embodiments, the pocket 120 may be made of a woven material with mixed strands of both hydrophobic and hydrophilic components to provide the moisture wicking properties of the material of the pocket 120.

In some embodiments, the pocket 120 may include an adhesive at a distal end of the pocket 120 away from an opening of the pocket. For example, the adhesive at the distal end of the pocket 120 may facilitate keeping the monitoring device 130 from moving around within the pocket 120. In some embodiments, one or more internal surfaces of the pocket 120 may be treated with an adhesive that binds over time to the monitoring device 130 such that it can be slid into the pocket 120 and then adhered into place.

In some embodiments, the pocket 120 may include a generally trapezoidal shape. For example, the opening end of the pocket 120 and the distal end of the pocket 120 (the end opposite the opening) may be generally parallel, and the other two sides of the quadrilateral of the pocket 120 may be non-parallel. For example, as illustrated by parallel lines 140a and 140b, the sides of the pocket 120 may narrow from the opening end to the distal end of the pocket 120. Such a trapezoidal shaped embodiment of the pocket 120 may facilitate the use of a monitoring device with a shape that is wider at one end and narrower at the other end. Furthermore, such a shape may facilitate a more snug or tight fit of the monitoring device 130 within the pocket 120. By providing a snug fit within the pocket 120, movement of the monitoring device 130 within the pocket 120 may be reduced, minimized, or completely removed.

In some embodiments, the pocket 120 may be sealed on two sides and both an opening end and a distal end may be open. In these and other embodiments, the two non-parallel sides of the quadrilateral may be sealed and the other two sides of the trapezoidal shape may be open. In these and other embodiments, the shape of the trapezoidal pocket 120 may retain the monitoring device 130 within the pocket 120.

In some embodiments, the pocket 120 may include a generally rectangular shape. In these and other embodiments, the pocket 120 may be sealed on three of the four sides, leaving the opening side of the pocket 120 open and the others being sealed. In these and other embodiments, the rectangular shape of the pocket 120 may be sized to receive the monitoring device 130 within the pocket 120.

In some embodiments, the adhesive film 110 may cover a first surface area of the skin and the pocket 120 may cover a second surface area of the skin (which may overlap a portion of the first surface area). The ratio of the two surface areas may vary, depending on the embodiment. For example, the second surface area may be one third or less of the first surface area, the second surface area may be between one fourth and one sixteenth of the first surface area, etc. In some embodiments, the ratio may be selected such that the moisture wicked away from the skin by the pocket 120 may have a sufficient surface area to dissipate that moisture into the air through the adhesive film 110. In some embodiments, the ratio may be selected to maintain sufficient contact with the skin (e.g., such that the monitoring device 130 does not peel away from the skin) while reducing or minimizing the amount of adhesive material used The monitoring device 130 may include any device that is battery powered and configured to monitor one or more biological properties of the subject. The monitoring device 130 may include any number and/or type of sensors, such as a microphone oriented towards the skin of the subject, an accelerometer, etc. In some embodiments, the pocket 120 may include one or more cutouts corresponding to one or more sensors of the monitoring device 130. For example, the pocket 120 may include a gap in material corresponding to the location of the microphone of the monitoring device 130. As another example, the pocket 120 may include gaps in material corresponding to ECG leads of the monitoring device 130. In some embodiments, the monitoring device 130 may include a protective coating, outer layer, or other material that protects the internal electrical components of the monitoring device 130 from being damaged by moisture (e.g., from sweat). For example, the monitoring device 130 may include a silicone material, or other moisture resistant or waterproof layer on the outside of the monitoring device 130.

In some embodiments, the pocket 120 may be shaped and configured to receive the monitoring device 130 in both a normal orientation and an inverted orientation. For example, one or more sensors of the monitoring device 130 may be oriented towards a body of a user of the monitoring device 130 in the normal orientation, and the sensors may be oriented away from the body in the inverted orientation. In both orientations, the wider end of the monitoring device 130 may be at the wider end of the trapezoidal shape of the pocket 120.

Figure 6:
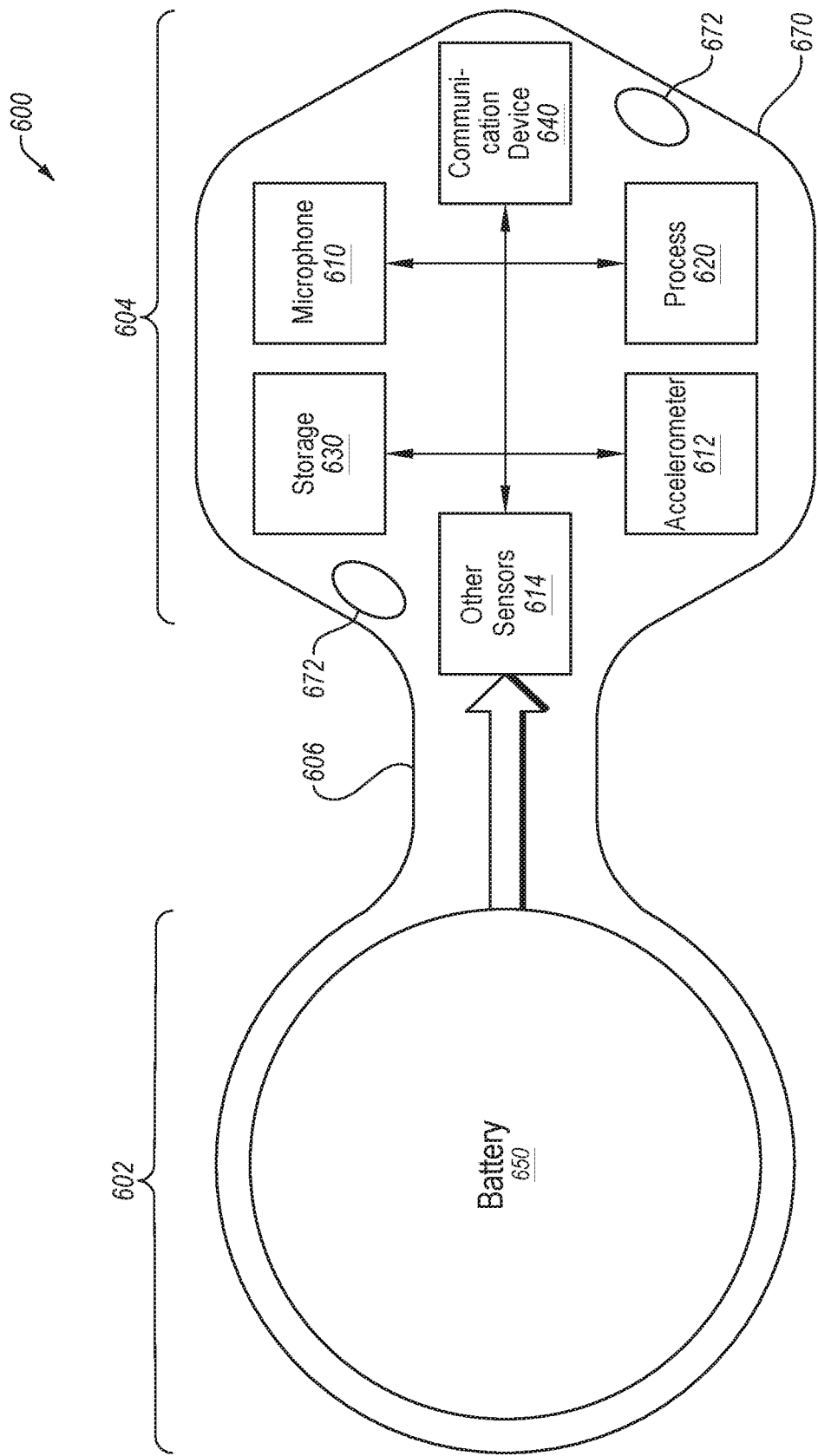
FIG. 6 includes an example monitoring device.

An example of the monitoring device 130 may be described with greater detail with reference to FIG. 6.

Modifications, additions, or omissions may be made to the adhesive device 100 without departing from the scope of the present disclosure. For example, the adhesive device 100 may include more or fewer elements than those illustrated in FIG. 1. As another example, the pocket 120 may take any shape that corresponds to various shapes of the monitoring device 130.

Figure 2:
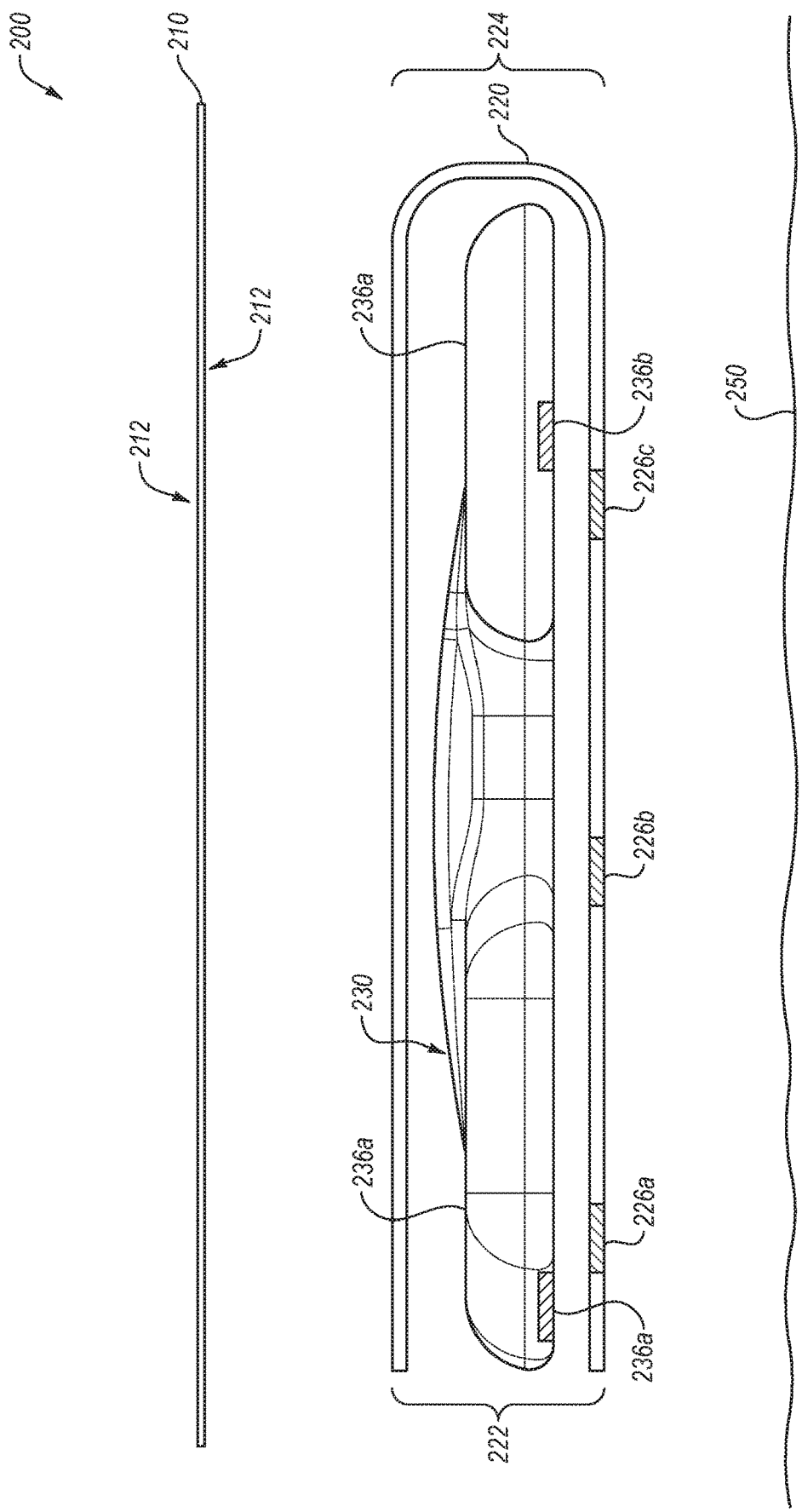
FIG. 2 illustrates an exploded side view of an example adhesive device.

FIG. 2 illustrates an exploded side view of an example adhesive device 200, in accordance with one or more embodiments of the present disclosure. The adhesive device 200 is not necessarily illustrated to scale, but rather, is illustrated such that the relative positions of the various components of the adhesive device 200 may be clearly observed. For example, for the adhesive device 200, an adhesive film 210 may be disposed farthest away from skin 250 of a subject. Beneath the adhesive film 210, a pocket 220 may envelope a monitoring device 230. The bottom part of the envelope 220 may be directly against the skin 250, and portions of the adhesive film 210 not covered by the pocket 220 may also be directly against the skin 250.

As illustrated in FIG. 2, the adhesive film 210 may include an adhesive side 214 and a non-adhesive side 212. The adhesive film 210 may be similar or comparable to the adhesive film 110 of FIG. 1.

The pocket 220 may include an opening end 222 and a distal end 224 opposite the opening end 222. The pocket 220 may be similar or comparable to the pocket 120 of FIG. 1.

In some embodiments, the pocket 220 may include one or more regions 226 (such as the regions 226a, 226b, and 226c) that may be different from the rest of the material of the pocket 220. The regions 226 may include a material that may capture and retain one or more biological samples from the subject. For example, the regions 226 may capture one or more skin cells of the subject, sweat droplets of the subject, etc. In some embodiments, the regions 226 may include an adhesive specifically designed to cling to skin cells (e.g., the adhesive for the regions 226 may be a stronger adhesive than the adhesive for the rest of the pocket 220). As another example, the regions 226 may include a compound that chemically bonds with or is otherwise attracted to certain molecules. For example, the regions 226 may include strongly hydrophilic cores that keep moisture molecules within the regions 226 rather than allowing them to be dissipated away from the regions 226. In some embodiments, the regions 226 may bond to components within sweat, such as molecules of interest related to one or more properties of sweat of the subject. For example, the regions 226 may include material to bond with by-products produced when the subject has been drinking ethanol, smoking tobacco, using another drug (such as marijuana, methamphetamines, cocaine, etc.), etc. that is located in the sweat of the subject. An example of such molecules and their detection is described in U.S. application Ser. No. 15/639,636 titled "OPERATION-VERIFYING WEARABLE VAPOR SENSOR," which is hereby incorporated by reference in its entirety. In some embodiments, when used for monitoring sweat, the adhesive device 200 may be positioned proximate a region of the body that is known to sweat, such as the wrist, on the chest near the armpit, near the ear canal, etc.

In some embodiments, the regions 226 may include a material that changes color based on the presence of one or more molecules of interest within the sweat of the subject. For example, if the subject has smoked, certain byproduct molecules may be produced in the sweat of the subject and the regions 226 may include molecules that change color based on the presence of the certain byproduct molecules in the sweat being wicked away from the skin 250 by the material of the pocket 220. In these and other embodiments, the monitoring device 230 may include one or more visual sensors positioned and configured to detect changes in color of the regions 226.

In some embodiments, the monitoring device 230 may include similar or comparable regions 236 (such as the regions 236a and/or 236b). The regions 236 may be configured to perform a similar or comparable function to the regions 226. For example, the regions 236 may capture and/or retain one or more of skin cells of the subject, sweat molecules or other samples given off from the subject. In some embodiments the regions 236 may be made of a different material, utilize a different adhesive, etc. In some embodiments, the regions 236 may include color-changing molecules embedded within the outer layer of the monitoring device 230 to detect the presence of various molecules as described herein.

Modifications, additions, or omissions may be made to the adhesive device 200 without departing from the scope of the present disclosure. For example, the adhesive device 200 may include more or fewer elements than those illustrated in FIG. 2. As another example, there may be any number or combination of the regions 226 and/or the regions 236.

Figure 3:
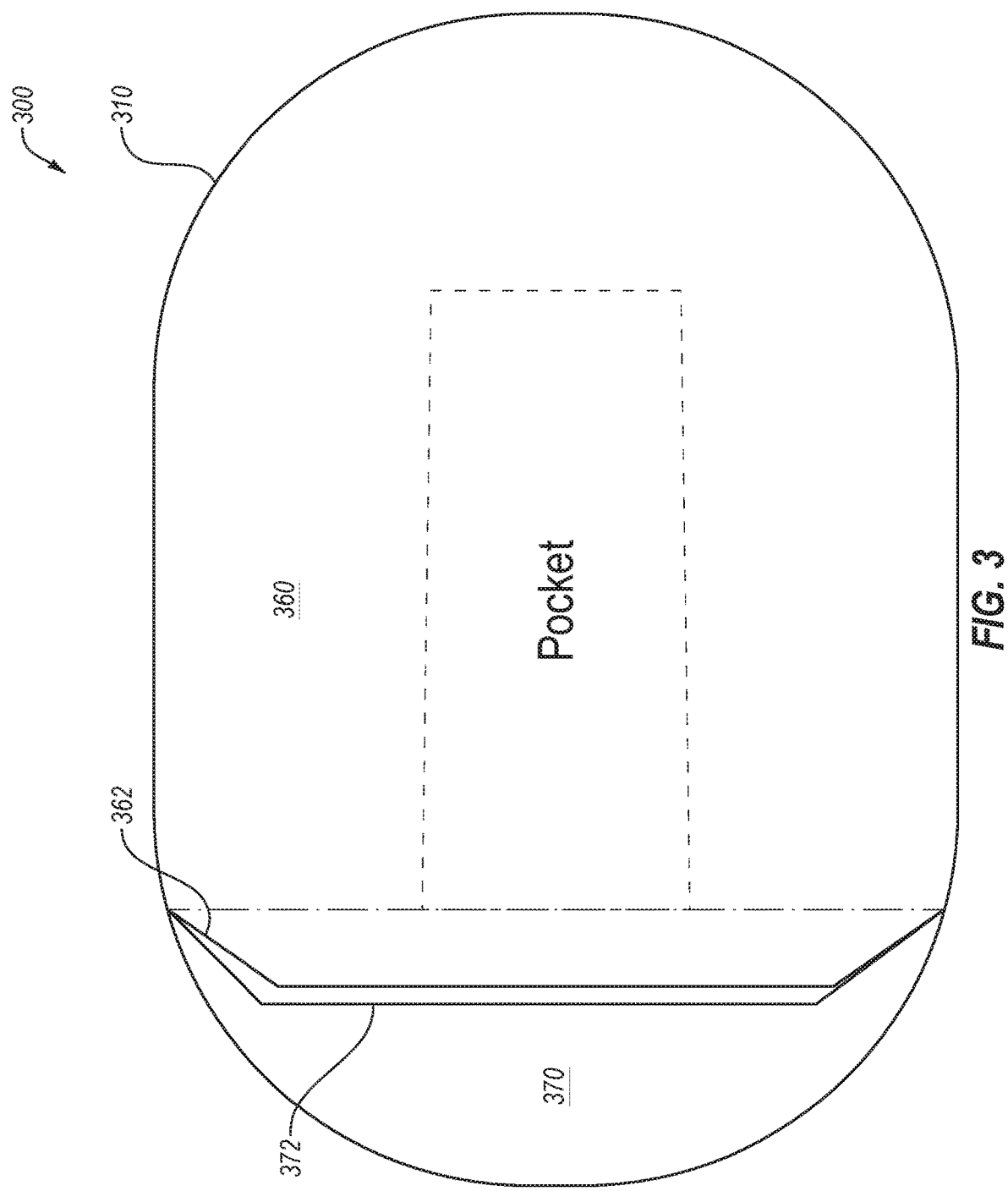
FIG. 3 illustrates an adhesive device with a backing.

FIG. 3 illustrates an adhesive device 300 with a backing, in accordance with one or more embodiments of the present disclosure. As illustrated in FIG. 3, the adhesive device 300 may include an adhesive film 310 and a pocket 320 that may be similar or comparable to the adhesive film 110/210 and the pocket 120/220 of FIGS. 1 and 2, respectively. In some embodiments the backing may include a first backing 360 and a second backing 370.

The backing, including the first backing 360 and the second backing 370 may be made of a material that is non-adhesive and able to protect the adhesive layer of the adhesive film 310 and/or the adhesive of the pocket 320 during shipping, handling, and before adhering the adhesive device 300 to skin of a subject. The backing may be removable such that when removed, the various adhesives are exposed such that the adhesive device 300 may be deployed.

In some embodiments, the first backing 360 may cover a majority of the adhesive film 310 and/or the majority of the pocket 320. In these and other embodiments, a user may remove the first backing 360 by pulling on a first pull tab 362 to peel away the first backing from the adhesive film 310. Removing the first backing 360 may expose an opening of the pocket 320 proximate the second backing 370 such that the user may continue to hold the adhesive device 300 via the region of the adhesive film 310 still covered by the second backing 370 when sliding a monitoring device (not shown) into the pocket 320. After the monitoring device is within the pocket 320, the user may adhere the adhesive device 300 to the skin of the subject beginning with the portion exposed by removing the first backing 360 and afterwards removing the second backing 370 by pulling the second pull tab 372.

Additionally or alternatively, the first backing 360 may be positioned such that it does not cover the opening of the pocket 320. In these and other embodiments, the second backing 370 may be removed exposing only a small amount of the adhesive film 310 while still exposing the opening of the pocket 320 such that the monitoring device may be disposed within the pocket 320. After the monitoring device is in place, the second backing 360 may be removed and the adhesive device 300 may be adhered to the skin of the subject.

Modifications, additions, or omissions may be made to the adhesive device 300 without departing from the scope of the present disclosure. For example, the adhesive device 300 may include more or fewer elements than those illustrated in FIG. 3. As another example, the backing may be divided into three or more components, or may be implemented as a single piece of backing.

Figure 4:
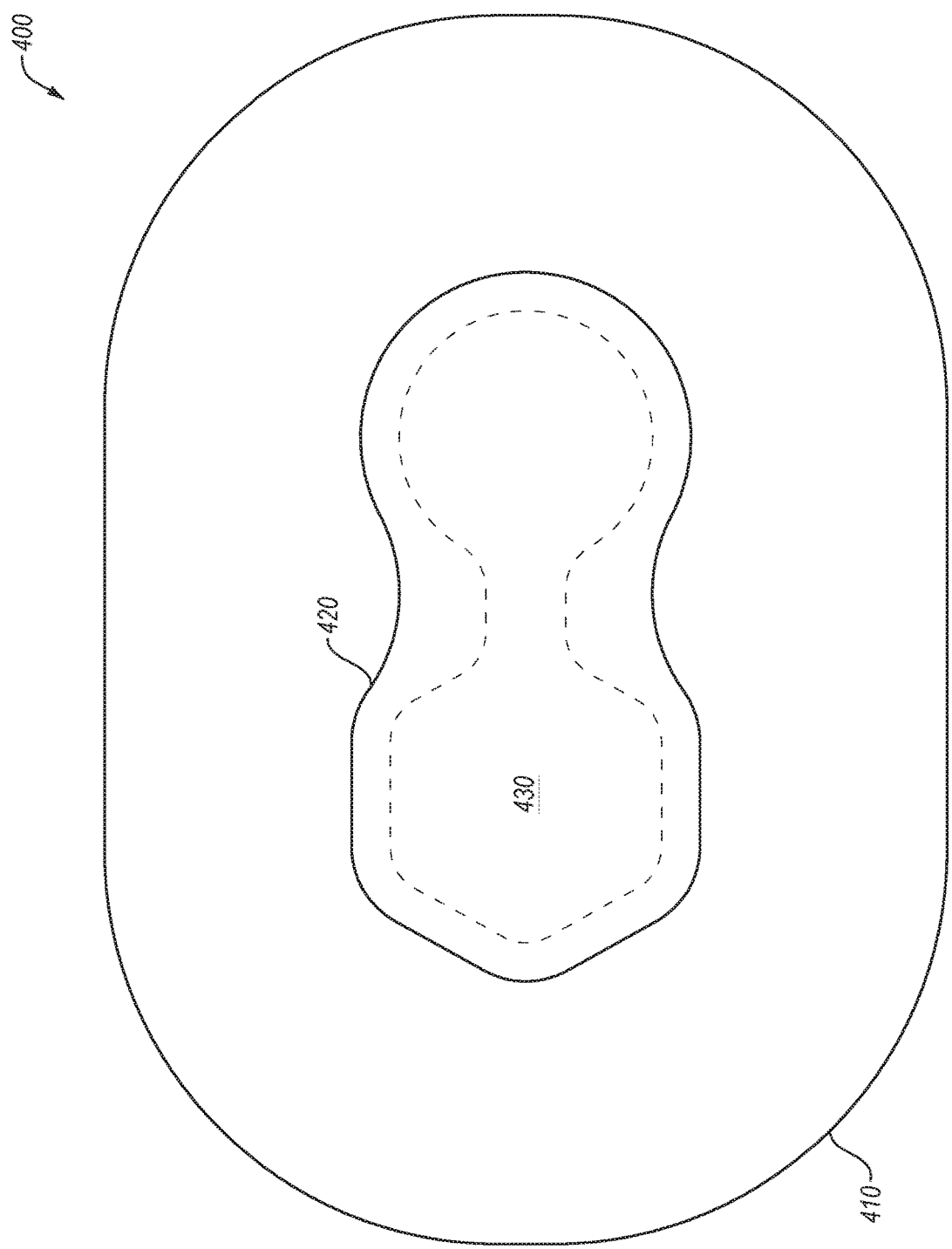
FIG. 4 illustrates another example adhesive device from a top down view.

FIG. 4 illustrates another example adhesive device 400 from a top down view, in accordance with one or more embodiments of the present disclosure. The adhesive device 400 may include an adhesive film 410, a bottom adhesive 420, and a monitoring device 430. The adhesive film 410 may be similar or comparable to the adhesive film 110/210 and the monitoring device 430 may be similar or comparable to the monitoring device 130/230 of FIGS. 1 and 2, respectively.

The bottom adhesive 420 may include a material with adhesive on both sides of the material. The bottom adhesive 420 may be coupled to the monitoring device 430. The bottom adhesive 420 adhered to the monitoring device 430 may be adhered to the adhesive film 410. The adhesive film 410 with the bottom adhesive 420 and the monitoring device 430 adhered thereto may be adhered to the skin of the subject.

In some embodiments, the bottom adhesive 420 may be made of a material similar or comparable to that used to create the pocket 120/220 of FIGS. 1 and 2. For example, the material may be a moisture wicking material. By using a moisture wicking material, the bottom adhesive 420 may prevent moisture, such as from sweat, from being trapped between the monitoring device 430 and the skin of the subject. For example, as described above, the monitoring device 430 may include a waterproof protective coating that may trap sweat or other moisture between the monitoring device 430 and the skin, which may be uncomfortable or unhealthy for the subject.

In some embodiments, the bottom adhesive 420 may be a similar or comparable shape to that of a profile of the monitoring device 430. Additionally or alternatively, the shape of the bottom adhesive 420 may be similar in shape but slightly larger than the monitoring device 430 (e.g., within 5-10 mm of the edge of the monitoring device). In some embodiments, the bottom adhesive 420 may include a larger surface area than that of the monitoring device (e.g., between 10 and 50% more surface area) to facilitate and enhance the moisture wicking capabilities of the bottom adhesive in wicking the moisture away from the skin of the subject.

In some embodiments, the bottom adhesive 420 may include a lip that extends beyond the device to reduce and/or mitigate the bottom adhesive 420 from lifting off of the skin as the subject moves. For example, if the bottom adhesive 420 were to be precisely the same size as the monitoring device 430, as the subject moved, because the monitoring device 430 is a solid object, the bottom adhesive 420 may begin to peel away from the skin, or the monitoring device 430 may peel away from the adhesive, which the lip may prevent.

Modifications, additions, or omissions may be made to the adhesive device 400 without departing from the scope of the present disclosure. For example, the adhesive device 400 may include more or fewer elements than those illustrated in FIG. 4. As another example, bottom adhesive 420 may take any shape or form.

Figure 5:
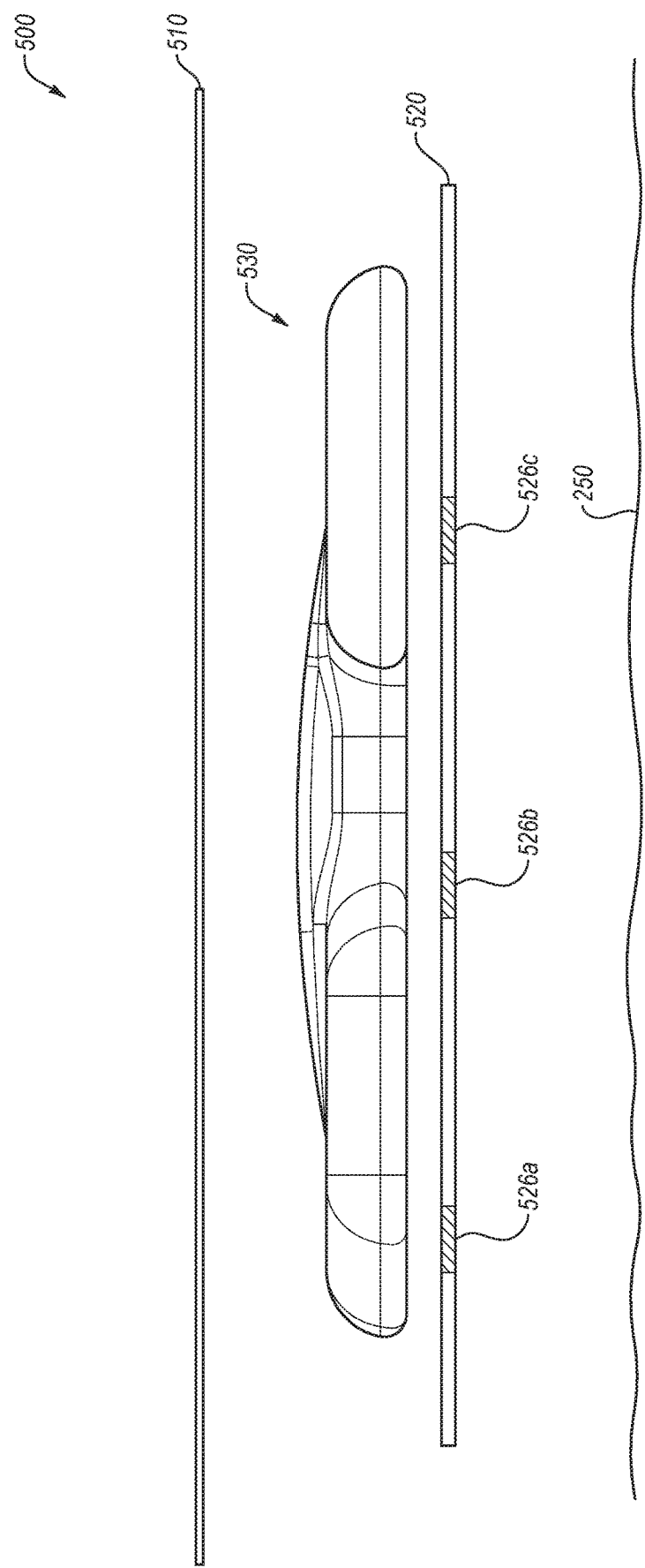
FIG. 5 illustrates an exploded side view of another example adhesive device.

FIG. 5 illustrates an exploded side view of another example adhesive device 500, in accordance with one or more embodiments of the present disclosure. The adhesive device 500 is not illustrated to scale, but rather, is illustrated such that the relative positions of the various components of the adhesive device 500 may be clearly observed. For example, for the adhesive device 500, an adhesive film 510 may be disposed farthest away from skin 550 of a subject. Beneath the adhesive film 510, a monitoring device 530 may be adhered to both the adhesive film 510 and a bottom adhesive 520. The bottom adhesive 520 may be directly against the skin 550, and portions of the adhesive film 510 not covered by the bottom adhesive 520 may also be directly against the skin 550. The adhesive film 510 may be similar or comparable to the adhesive films 110/210/410 of FIGS. 1, 2, and 4, respectively. The monitoring device 530 may be similar or comparable to the monitoring device 130/230/430 of FIGS. 1, 2, and 4, respectively, including the regions 236 of FIG. 2, although corresponding elements are not illustrated in FIG. 5.

The bottom adhesive 520 may be similar or comparable to the bottom adhesive 410 of FIG. 4. For example, the bottom adhesive 520 may be adhered to the monitoring device 530, and any portion of the bottom adhesive 520 larger than the monitoring device 530 may adhere to the adhesive film 510. The bottom adhesive 520 may additionally be adhered to the skin 550 of the subject.

The bottom adhesive 520 may include regions 526 (such as the regions 526a, 526b, and 526c) that may be similar or comparable to the regions 226 of FIG. 2. For example, the regions 526 may be configured to capture and retain any of skin cells of the subject, sweat from the subject, molecules within the sweat of the subject, etc., including combinations thereof.

Modifications, additions, or omissions may be made to the adhesive device 500 without departing from the scope of the present disclosure. For example, the adhesive device 500 may include more or fewer elements than those illustrated in FIG. 5. As another example, there may be any number or combination or the regions 226.

FIG. 6 includes an example monitoring device 600, in accordance with one or more embodiments of the present disclosure. The monitoring device 600 may be configured to monitor one or more properties of the subject while disposed proximate the subject via an adhesive device consistent with the present disclosure.

The monitoring device 600 may include a first lobe 602 and a second lobe 604 connected by a band 606. In some embodiments, the first lobe 602 may be narrower than the second lobe 604. The first lobe 602 may have a generally circular shape and the second lobe 604 may have a generally hexagonal shape, although any shape may be used.

Functionally, the monitoring device 600 may include a microphone 610, an accelerometer 612, other sensors 614, a processor 620, a storage 630, a communication device 640, a battery 650, a communication bus 660, and one or more regions 672 (which may be similar or comparable to the regions 236 of FIG. 2).

The microphone 610 may be used to record sound and may be oriented to face the skin of the subject. While the term microphone is used, it will be appreciated that term includes any type of acoustic sensor that may be configured to detect sound waves and convert them into a readable signal such as an electronic signal. For example, a piezoelectric transducer, a condenser microphone, a moving-coil microphone, a fiber optic microphone, a MicroElectrical-Mechanical System (MEMS) microphone, etc. or any other transducer may be used to implement the microphone 610.

The accelerometer 612 may be used to measure acceleration of at least a portion of the subject, such as the subject's chest, based on the monitoring device 600 being adhered via an adhesive device to the portion of the subject. The recorded acceleration may be processed to extract features that may be indicative (or not) of the various behaviors. For instance, when the subject sneezes, the subject's body (e.g., chest) upon which the monitoring device 600 is adhered may move violently. The violent movement of the subject's body (e.g., chest) may be identified in the acceleration recorded by the accelerometer 612. In some embodiments, the accelerometer 612 may be used to measure the orientation of the body of the subject, such as whether they are walking, lying down, etc.

The other sensors 614 may include any number of other sensors such as a gyro sensor, an oxygen saturation sensor, a thermometer, a photoplethysmography (PPG) sensor, an ECG sensor, an electrodermal activity (EDA) sensor, etc. or any combinations thereof. Any other of a variety of sensors may also be associated with the monitoring device 600. A gyro sensor may be used to measure angular velocity of at least a portion of the subject, such as the chest of subject. An oxygen saturation sensor may be used to record blood oxygenation of the subject to generate a blood oxygenation level signal of the subject. A thermometer may be used to record temperatures associated with the subject, including skin temperature and/or core body temperature. A PPG sensor may be used to record blood flow of the subject. An ECG sensor may be used to measure electrical activity of the subject's heart to determine the subject's heart rate and/or other parameters. An EDA sensor may be used to measure EDA of the subject's skin. A volatile organic compound (VOC) detector may be used to detect various organic molecules that may be coming off of a subject or their sweat. An optical sensor may be used to monitor or detect changes in color, such as changes in skin coloration, changes in adhesive coloration, etc. Additionally or alternatively, a spectrometer may measure electromagnetic (EM) radiation and may be configured to detect variations in reflected EM radiation. For example, such a sensor may detect changes in color in a molecule exposed to multi-spectral light (e.g., white light), and/or may detect other changes in reflected EM radiation outside of the visible spectrum (e.g., interaction with ultra-violet rays, etc.).

The processor 620 may include any device or component configured to monitor and/or control operation of the monitoring device 600. For example, the processor 620 may retrieve instructions from the storage 630 and execute those instructions. As another example, the processor 620 may read the signals generated by the sensors (e.g., the microphone 610, the accelerometer 612, and/or the other sensors 614) and may store the readings in the storage 630 or instruct the communication device 640 to send the readings to another electronic device. In some embodiments, the processor 620 may include an arithmetic logic unit, a microprocessor, a general-purpose controller, or some other processor or array of processors, to perform or control performance of operations as described herein. The processor 620 may be configured to process data signals and may include various computing architectures including a complex instruction set computer (CISC) architecture, a reduced instruction set computer (RISC) architecture, or an architecture implementing a combination of instruction sets. Although illustrated as a single processor 620, multiple processor devices may be included and other processors and physical configurations may be possible. The processor 620 may be configured to process any suitable number format including, but not limited to two's compliment numbers, integers, fixed binary point numbers, and/or floating point numbers, etc. all of which may be signed or unsigned. In some embodiments, the processor 620 may perform processing on the readings from the sensors prior to storing and/or communicating the readings. For example, raw audio data may be converted into another format before storing and/or communicating the readings from the microphone 610.

The storage 630 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 620. By way of example such computer-readable storage media may include non-transitory computer-readable storage media including Random Access Memory (RAM), Read-Only Memory (ROM), Electrically Erasable Programmable Read-Only Memory (EEPROM), flash memory devices (e.g., solid state memory devices), or any other storage medium which may be used to carry or store desired program code in the form of computer-executable instructions or data structures and which may be accessed by a general-purpose or special-purpose computer. In some embodiments, the storage 630 may also include volatile memory, such as a dynamic random access memory (DRAM) device, a static random access memory (SRAM) device, or the like. Combinations of the above may also be included within the scope of computer-readable storage media. Computer-executable instructions may include, for example, instructions and data configured to cause the processor 620 to perform a certain operation or group of operations. In some embodiments, the storage 630 may store the readings from the sensors.

The communication device 640 may include any device or component that facilitates communication with a remote device, such as a mobile device of the subject, a remote server, or any other electronic device. For example, the communication device 1440 may include an RF antenna, an IR receiver, a Wi-Fi chip, a Bluetooth® chip, a cellular chip, near field communication (NFC) chip, or any other communication device.

The battery 650 may include any device or component configured to provide power to the monitoring device 600 and/or the components thereof. For example, the battery 650 may include a rechargeable battery, a disposable battery, etc. In some embodiments, the monitoring device 600 may include circuitry, electrical wires, etc. to provide power from the battery 650 to the other components of the monitoring device 600. In some embodiments, the battery 650 may include sufficient capacity such that the monitoring device 600 may operate for days, weeks, or months without having the battery changed or recharged. For example, the monitoring device 600 may be configured to operate for at least two months without having the battery 650 charged or replaced.

In some embodiments, the battery 650 may be located in the first lobe 602 and the other components of the monitoring device 600 may be in the second lobe 604. The monitoring device 600 may include wires or other electrical connections spanning the band 606 such that the electrical power from the battery 650 in the first lobe 602 may be provided to the other components in the second lobe 604.

The communication bus 660 may include any connections, lines, wires, or other components facilitating communication between the various components of the monitoring device 600. The communication bus 660 may include one or more hardware components and may communicate using one or more protocols. Additionally or alternatively, the communication bus 660 may include wire connections between the components.

The regions 672 may include one or more components or materials configured to capture and retain one or more biological samples from the subject. For example, the regions 672 may be configured to capture and retain sweat droplets, skin cells, etc. of the subject. Additionally or alternatively, the regions 672 may be configured to capture and retain one or more molecules of interest within the sweat or other biological samples from the subject.

In some embodiments, the monitoring device 600 may operate in a similar or comparable manner to the embodiments described in U.S. application Ser. No. 16/118,242, which is hereby incorporated by reference in its entirety.

In some embodiments, the monitoring device 600 may be implemented as a relatively cheap wearable electronic device. In these and other embodiments, the monitoring device 600 may have a relatively constrained power supply (e.g., a relatively small battery compared to some computing devices) and/or a relatively constrained network connection (e.g., a Bluetooth connection on the order of tens of megabits per second (Mbit/s)). In such an embodiment of the monitoring device 600, it may be too power- and/or processor-intensive to process the data from the sensors locally on the monitoring device 600 using standard algorithms, and/or too bandwidth-intensive to upload the data to a remote server for processing. Additionally, it may be overly power-intensive to continuously record audio data using the microphone 610. In these and other embodiments, various approaches may be taken to extend the battery life, constrain the data collected, etc. to extend the usability and life of the monitoring device 600.

Figure 7:
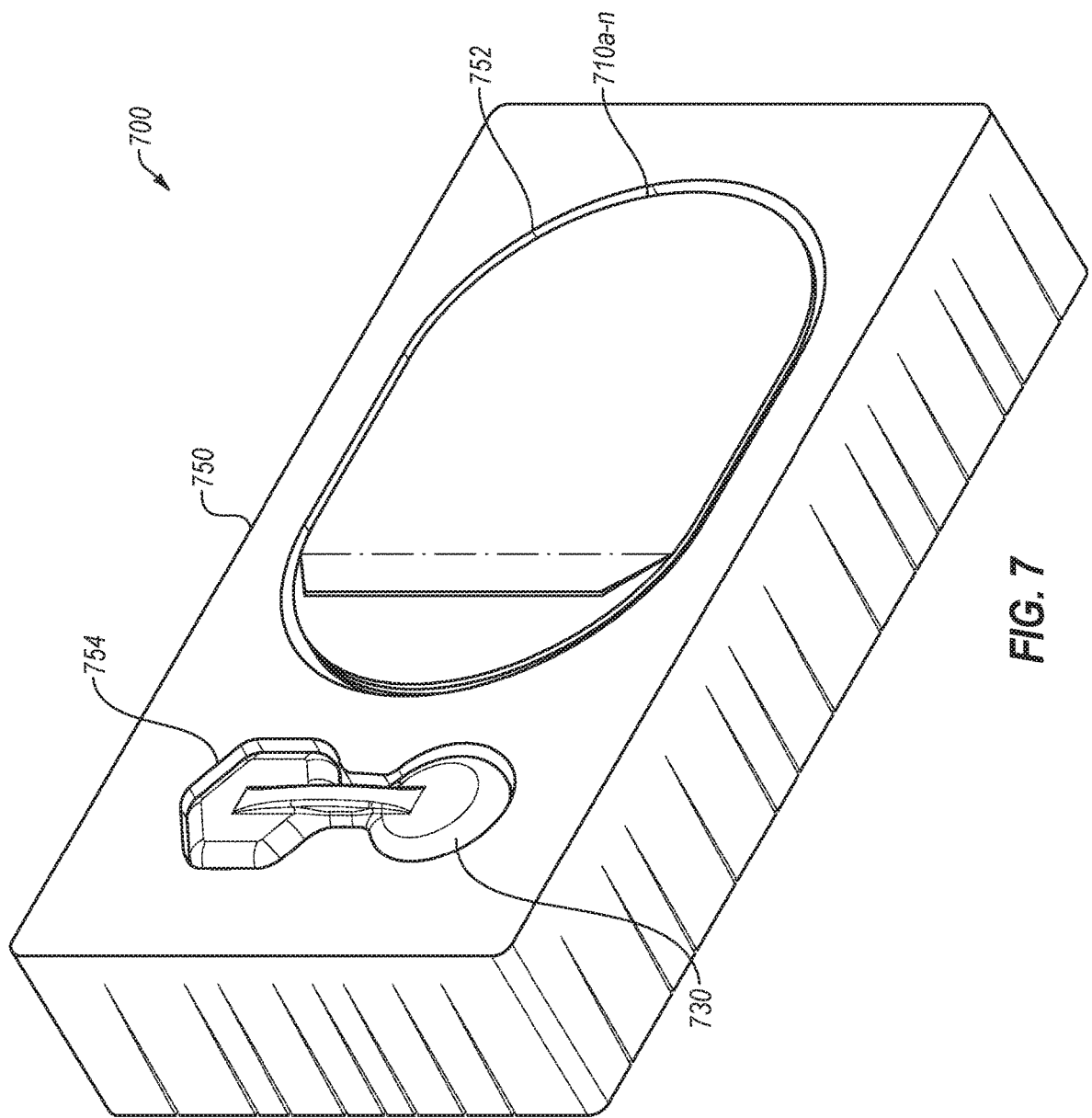
FIG. 7 illustrates an example package including an example monitoring device and example adhesive devices.

FIG. 7 illustrates an example package 700 including an example monitoring device 730 and example adhesive devices 710 (such as the adhesive devices 710*a-n*), in accordance with one or more embodiments of the present disclosure. In some embodiments, a subject may receive the package 700 such that the subject can use the monitoring device 730 for a predefined period of time (e.g., two weeks, four weeks, six weeks, two months, three months, etc.) with a new adhesive device 710 for each week. Using the package 700, the subject may remove the old adhesive device and place the monitoring device in a new adhesive device each week during the predefined period of time. In some embodiments, the package 700 may be utilized to distribute the adhesive devices 710 and/or the monitoring device 730 to consumers such as the subject.

The package 700 may include a tray 750 with a first space 752 for holding the adhesive devices 710 and a second space 754 for holding the monitoring device 730. The tray 750 may be made of any material used in packaging, such as plastic, cardboard, etc.

In some embodiments, the package 700 may include a return package via which the subject may return the monitoring device 730 and/or one or more of the adhesive devices 710*a-n*.

Figure 8:
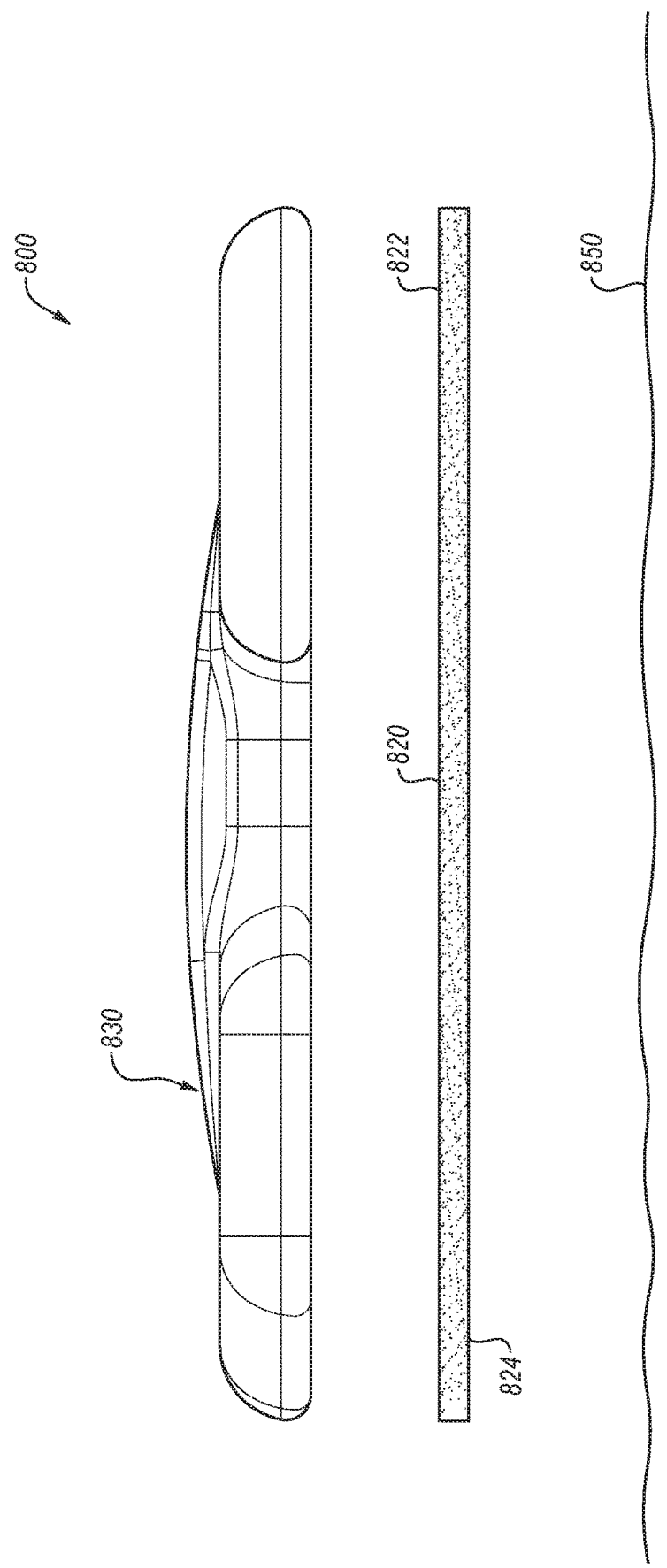
FIG. 8 illustrates an exploded side view of another example adhesive device and associated medical device.

FIG. 8 illustrates an exploded side view of an example system 800 including an adhesive device 820 and an associated medical device 830. The adhesive device 820 may be used to adhere the medical device 830 to skin 850 of a user.

The adhesive device 820 may include a first adhesive surface 822 which may be configured to adhere to the medical device 830. In some embodiments, the material of the first adhesive surface 822 may be configured to adhere to a material of which the medical device 830 is coated. For example, if the medical device 830 includes a silicone coating, the material of the first adhesive surface 822 may be configured to adhere to silicone.

The adhesive device 820 may include a second adhesive surface 824 which may be configured to adhere to the skin 850. In some embodiments, the material of the second adhesive surface 824, and/or the adhesive device 820 generally, may be selected to be compatible with the skin 850.

In some embodiments, the adhesive device 820 may be configured to cling to and/or retain skin cells and/or sweat such that upon removal of the adhesive device 820 from the skin 850, a certain number of skin cells and/or sweat molecules are retained on the adhesive device 820.

In some embodiments, the adhesive device 820 may be the same shape as the medical device 830. For example, if the medical device 830 includes two lobes with a connecting portion, the adhesive device 820 may include a corresponding shape. In these and other embodiments, the shape may be approximately the same, for example, if the medical device 830 includes a hexagonal-shaped lobe and a circular-shaped lobe, the adhesive device 820 may include two circular-shaped lobes.

Modifications, additions, or omissions may be made to the system 800 without departing from the scope of the present disclosure. For example, the system 800 may include more or fewer elements than those illustrated in FIG. 8. As another example, the adhesive device 800 may include any of the features, properties, etc. of any of the other adhesive devices of the present disclosure.

Figure 9:
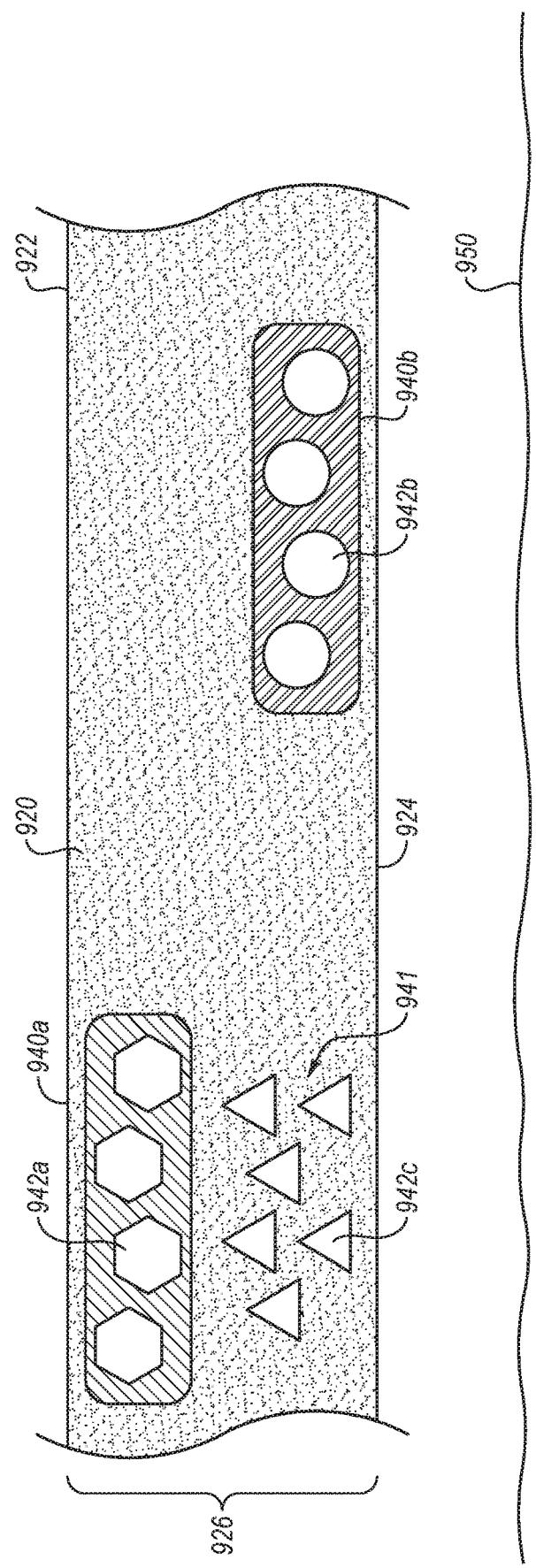
FIG. 9 illustrates a side of the adhesive device of FIG. 8.

FIG. 9 illustrates a side of an example adhesive device 920 that may be similar or comparable to the adhesive device 820 of FIG. 8. The adhesive device 920 may include a first adhesive surface 922 and a second adhesive surface 924 that may be similar or comparable to the adhesive surfaces 822 and 824, respectively, of FIG. 8. As illustrated in FIG. 9, the adhesive device 920 may include one or more detector compounds 942 configured to detect target molecules (not illustrated). The detector compounds 942 may be disposed within an intermediate region 926 between the first adhesive surface 922 and the second adhesive surface 924.

In some embodiments, the detector compounds 942 may be embedded within a layer of material 940 such that the adhesive device 820 may include one or more such layers of material 940. For example, as illustrated in FIG. 9, the adhesive device 920 may include a first layer of material 940*a* with detector compounds 942*a* configured to detect a first target molecule embedded within the first layer of material 940*a*, and a second layer of material 940*b* with detector compounds 942*b* configured to detect a second target molecule embedded within the second layer of material 940*b*. Additionally or alternatively, the adhesive device 920 may include a region 941 of detector compounds 942*a* embedded within a material of the adhesive device 920 generally. In some embodiments, the adhesive device may include one or more layers of material 940 as well as one or more regions 941 with detector compounds 942 in the material of the adhesive device 920 generally.

In some embodiments, the detector compounds 942 of a certain target molecule may be localized in a particular region of the adhesive device 920, and/or of a particular layer of material 940 of the adhesive device 920. Additionally or alternatively, the detector compounds 942 may be dispersed throughout the adhesive device 920. In some embodiments, the detector compounds 942 may be located on the first adhesive surface 922 such that the detector compounds 942 may be in close proximity to an associated medical device. Additionally or alternatively, the detector compounds 942 may be located on the second adhesive surface 922 such that the detector compounds 942 may be in close proximity to the skin of the user. For example, some detector compounds 942 and or regions 941 may span from the first adhesive surface 922 to the second adhesive surface 924.

The detector compounds 942 may be configured to change in response to the target molecule being in the presence of the corresponding detector compound. In some embodiments, the change may include a change in color (e.g., the detector compound may change its shape to interact differently with light such that the detector compound appears as a different color). In some embodiments, the change may be triggered by the detector compound 942 forming a bond with the target molecule. Other examples of change may include a change in pH, a change in temperature, a change in electrical property such as conductivity, current, or capacitance, etc.

In some embodiments, the target molecule may include molecule as described as being monitored for or detected herein, such as metabolites or other byproducts generated by the body of a nicotine, alcohol, marijuana, cocaine, methamphetamines, etc. In some embodiments, the target molecules may include sweat generally, and/or skin cells. In these and other embodiments the detector molecules 942 may be configured to cling to and/or retain sweat or skin cells.

Modifications, additions, or omissions may be made to the adhesive device 920 without departing from the scope of the present disclosure. For example, the adhesive device 920 may include more or fewer elements than those illustrated in FIG. 9. As another example, there may be any number of layers and/or regions, and any number of detector compounds configured to interact with any number of target molecules.

Figure 10:
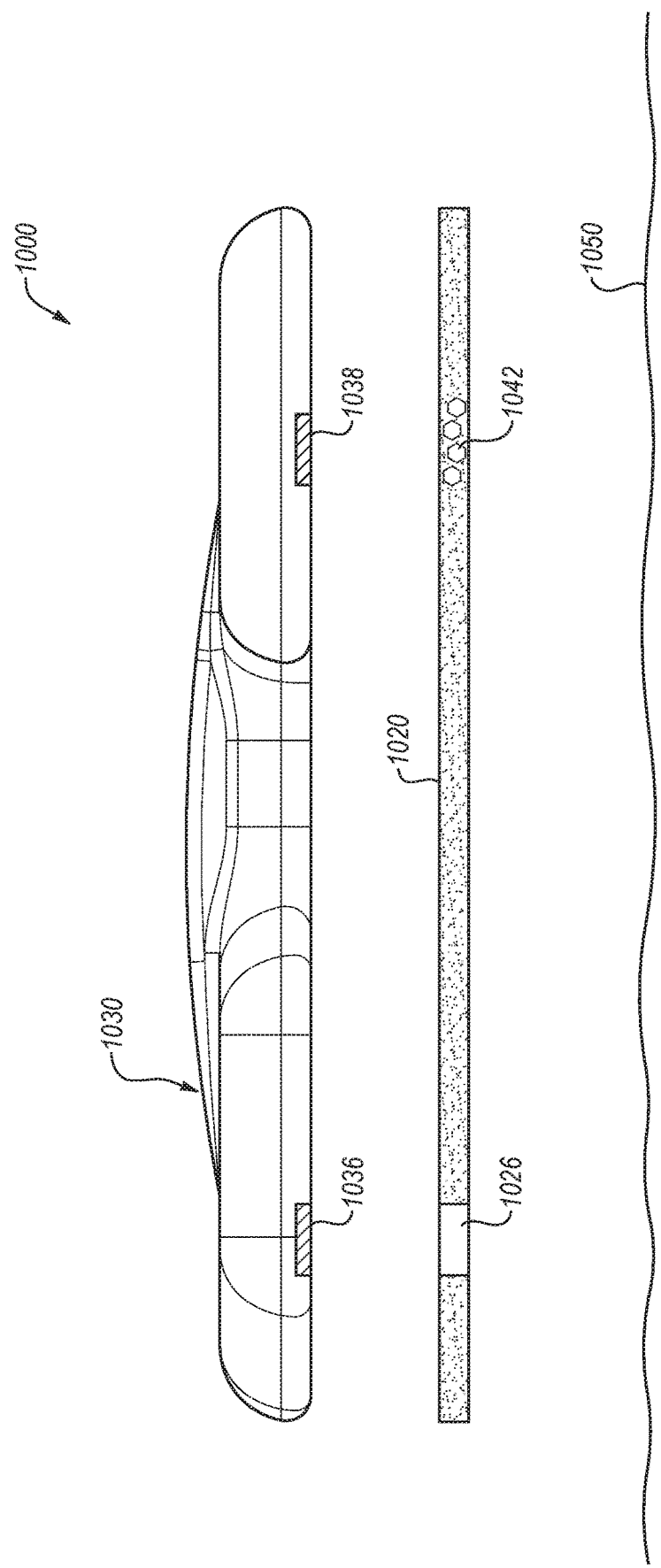
FIG. 10 illustrates an exploded side view of an additional example adhesive device and associated medical device, all arranged in accordance with at least one embodiment described herein.

FIG. 10 illustrates an exploded side view of a system 1000 including an example adhesive device 1020 and an associated medical device 1030 adhered to the skin 1050 of a user. As illustrated in FIG. 10, the medical device 1030 may include one or more sensors such as the sensors 1036 and 1038. As described herein, the sensors 1036 and/or 1038 may be positioned to correspond to certain aspects of the adhesive device 1020. The adhesive device 1020 may be similar or comparable to the adhesive devices described herein, and the medical device 1030 may be similar or comparable to the medical devices described herein.

As illustrated in FIG. 10, the sensor 1036 may correspond to a gap in material 1026 in the adhesive device 1020. For example, the sensor 1036 may be configured to perform an EKG and the gap in material 1036 may permit the sensor 1036 to operate as an EKG lead.

In some embodiments, the medical device 1030 may include a sensor, such as the sensor 1038, configured to detect a change in a detector compound 1042. In these and other embodiments, if the detector compound 1042 is localized to a certain region of the adhesive device 1020, the sensor 1038 may be positioned proximate the certain region. In some embodiments, the sensor 1038 may be configured to detect changes in light interactions (e.g., changes in color). In these and other embodiments, the sensor 1038 may be configured to detect, at the medical device 1030, whether or not the target molecule is present. For example, if the detector compound 1042 were detecting the presence of a by-product of alcohol in the sweat coming off of the skin 1050 of the user, the detector compound 1042 may change color when the by-product is detected. The sensor 1038 may be configured to periodically monitor for changes in color. Based on the alcohol by-product causing a change in color, the sensor 1038 may detect the change in color, and thus, the presence of the by-product.

In some embodiments, rather than being monitored by the sensor 1038 at the medical device 1030, the adhesive device 1020 may retain sweat, epithelial cells, skin cells, hair, sebum, hormones, and/or other material such that after the adhesive device 1020 is removed from the skin 1050, the adhesive device 1020 may be provided to a third party, such as a provider of the medical device 1030, a physician, etc.

The third party may perform analysis on the material retained at the adhesive device and/or on the adhesive device itself. For example, a spectral analysis may be performed on the adhesive device 1020 to determine the presence of certain colors corresponding to certain target molecules. As another example, DNA sequencing may be performed on DNA material extracted from the skin cells. As an additional example, the sebum and/or sweat may be analyzed to detect byproducts of certain drugs. Any other analyses may be performed on the material retained with the adhesive device.

In some embodiments, upon removal of the adhesive device 1020, the adhesive device 1020 may be combined with a stabilizing and/or preserving media to preserve the cells prior to arrival at the third party for processing. For example, such a stabilizing media may include a solution in which the adhesive is placed, such as a ringer solution or other isotonic solution. As another example, the stabilizing media may include a lysing agent for opening the cells and exposing the DNA and a stabilizing agent to stabilize the DNA. As an additional example, the stabilizing media may include a gel or paste into which the adhesive device 1020 is placed or that may be spread on the adhesive device 1020. In some embodiments, the adhesive device 1020 may include such stabilizing agents embedded within the adhesive device 1020, such as a layer or region within the adhesive device 1020.

Modifications, additions, or omissions may be made to the system 1000 without departing from the scope of the present disclosure. For example, the system 1000 may include more or fewer elements than those illustrated in FIG. 10. As another example, there may be any number of sensors in the medical device 1030, any number of gaps in material 1026 in the adhesive device, and/or any number of layers and/or regions of detector compounds 1042.

The present disclosure is not to be limited in terms of the particular embodiments described herein, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An adhesive device, comprising:
   one or more layers of material, the one or more layers including:
   a first adhesive surface configured to be adhered to skin of a user;
   a second adhesive surface opposite the first adhesive surface and configured to be adhered to a medical device; and
   an intermediate region of the one or more layers of material between the first adhesive surface and the second adhesive surface, the intermediate region including a detector compound embedded in the one or more layers of material and configured to change based on interaction of the detector compound with a target molecule.

2. The adhesive device of claim 1, further comprising a second detector compound embedded within the one or more layers of material and configured to change based on interaction of the second detector compound with a second target molecule different from the target molecule.

3. The adhesive device of claim 1, wherein the change of the detector compound includes changing interaction with electromagnetic radiation.

4. The adhesive device of claim 3, wherein the change in interaction with the electromagnetic radiation includes changing a visible color of light reflected by the detector compound when exposed to multi-wavelength light.

5. The adhesive device of claim 1, wherein the change of the detector compound includes changing an electrical property including at least one of conductance or capacitance.

6. The adhesive device of claim 1, wherein the medical device to which the adhesive device is adhered is configured to detect the change of the detector compound.

7. The adhesive device of claim 1, wherein the target molecule includes a byproduct eluted through sweat for at least one of nicotine, ethanol, marijuana, cocaine, or methamphetamines.

8. The adhesive device of claim 1, wherein a material of the first adhesive surface is configured to cling to and retain one or more of epithelial, skin, or hair to be used in DNA sequencing.

9. The adhesive device of claim 1, wherein the adhesive device includes a void in material corresponding to a sensor of the medical device.

10. A system comprising:
a medical device configured to be worn on skin of a user;
an adhesive configured to adhere the medical device to the skin of the user, comprising:
one or more layers of material;
a first adhesive surface at one outer end of the one or more layers of material and configured to be adhered to skin of the user;
a second adhesive surface at an opposite end of the one or more layers of material from the first adhesive surface and configured to be adhered to the medical device; and
an intermediate region of the one or more layers of material between the first adhesive surface and the second adhesive surface, the intermediate region including a detector compound embedded in a first layer of material of the one or more layers of material, the detector compound configured to change based on interaction of the detector compound with a target molecule.

11. The system of claim 10, the adhesive further comprising a second detector compound embedded in a second layer of material, the second detector compound configured to change based on interaction of the second detector compound with a second target molecule different from the target molecule.

12. The system of claim 10, wherein the change of the detector compound includes changing interaction with electromagnetic radiation.

13. The system of claim 12, wherein the change in interaction with the electromagnetic radiation includes changing a visible color of light reflected by the detector compound when exposed to multi-wavelength light.

14. The system of claim 10, wherein the medical device to which the adhesive device is adhered further comprises a sensor configured to detect the change of the detector compound.

15. The system of claim 10, wherein the target molecule includes a byproduct eluted through sweat for at least one of nicotine, ethanol, marijuana, cocaine, or methamphetamines.

16. The system of claim 10, wherein a material of the first adhesive surface is configured to cling to and retain one or more of epithelial, skin, or hair to be used in DNA sequencing.

17. The system of claim 10, wherein the change of the detector compound includes changing an electrical property including at least one of conductance or capacitance.

18. The system of claim 10, wherein the adhesive device includes a void in material corresponding to a sensor of the medical device.

19. An adhesive configured to adhere a medical device to skin of a user comprising:
one or more layers of material;
a skin-facing adhesive surface at an outer end of the one or more layers of material;
a device-facing adhesive surface at an opposite end of the one or more layers of material from the skin-facing adhesive surface; and
a detector compound embedded in a first layer of material of the one or more layers of material, the detector compound configured to change based on interaction of the detector compound with a target molecule.

20. The adhesive of claim 19, further comprising a second detector compound embedded in a second layer of the one or more layers of material, the second detector compound configured to change based on interaction of the second detector compound with a second target molecule different from the target molecule.

* * * * *